United States Patent [19]

Meinershagen

[11] Patent Number: 4,836,781

[45] Date of Patent: Jun. 6, 1989

[54] DENTAL TOOL WITH DUAL RESTORATION MATERIAL RETAINERS

[75] Inventor: Charles I. Meinershagen, Redding, Calif.

[73] Assignee: NewTech Products, Inc., Palo Cedro, Calif.

[21] Appl. No.: 148,839

[22] Filed: Jan. 27, 1988

[51] Int. Cl.[4] .............................................. A61C 3/00
[52] U.S. Cl. .................................................. 433/141
[58] Field of Search ............... 433/141, 150, 152, 155, 433/156

[56] References Cited

U.S. PATENT DOCUMENTS 2,245,291  6/1941  Myerson ............................. 433/141
4,060,897  12/1977  Greenstein ......................... 433/141

*Primary Examiner*—Robert Peshock
*Attorney, Agent, or Firm*—Townsend & Townsend

[57] ABSTRACT

A dental tool for assisting in cavity repair in two adjacent teeth by facilitating removal of matrix bands therefrom after installation of filler restoration material.

The tool includes a shank terminating in a bifurcated end portion, each branch of the bifurcated end portion terminating in a working surface having an inner edge. The inner edges of the working surfaces are separated by a gap having a width sufficiently large to accommodate a dental matrix band and sufficiently narrow to enable the working surfaces to maintain tight common interproximal contact with the filler restoration material in adjacent teeth.

4 Claims, 2 Drawing Sheets

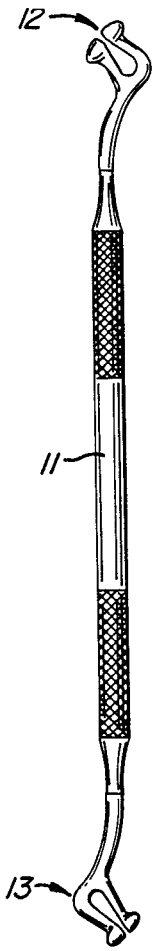
FIG._1.
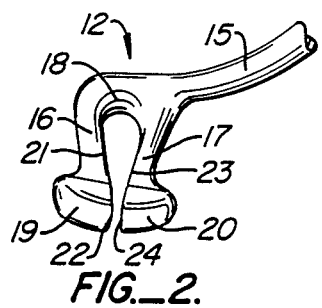
FIG._2.
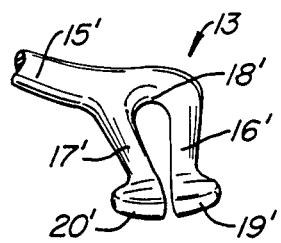
FIG._3.
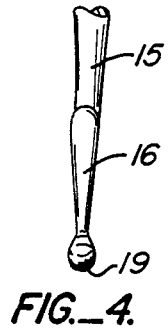
FIG._4.
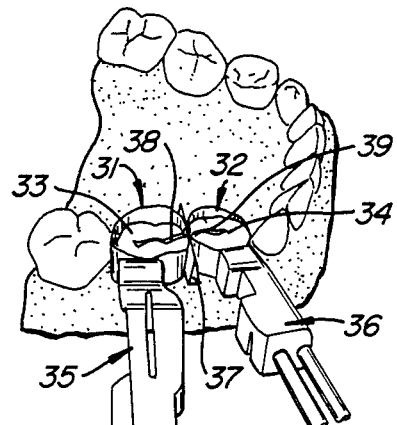
FIG._5A.
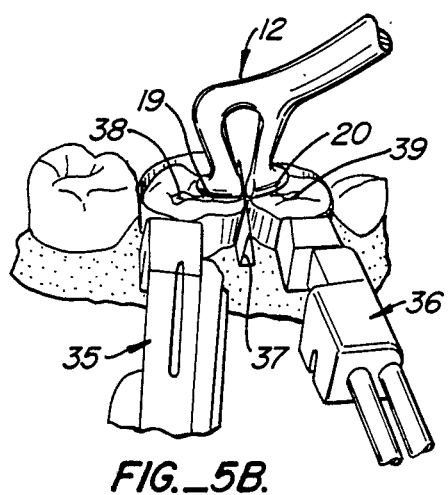
FIG._5B.
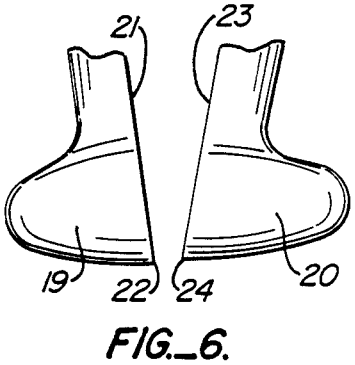
FIG._6.

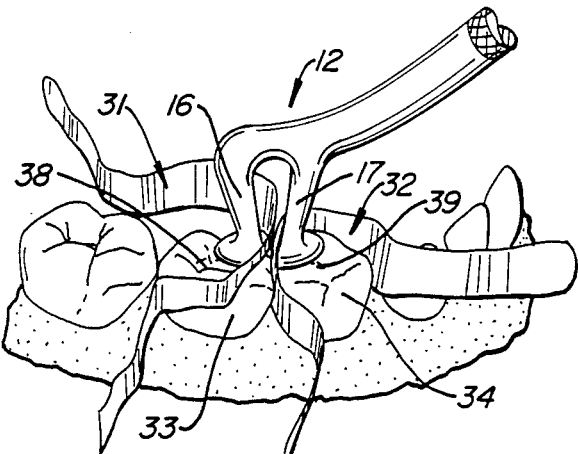
FIG._5C.
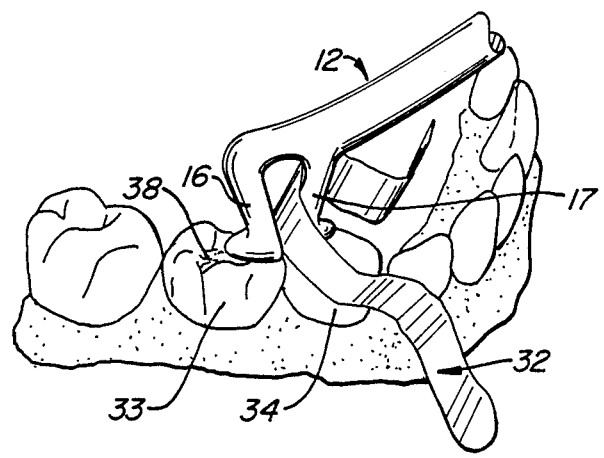
FIG._5D.
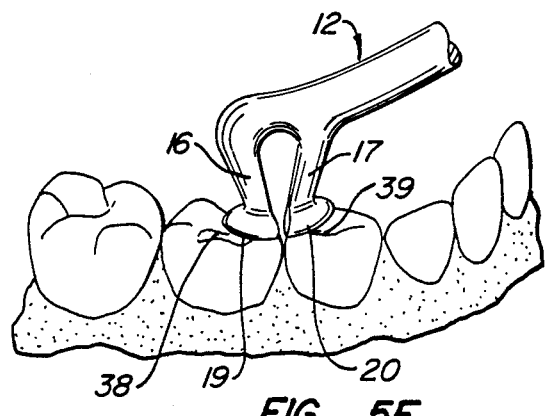
FIG._5E.

DENTAL TOOL WITH DUAL RESTORATION MATERIAL RETAINERS

BACKGROUND OF THE INVENTION

This invention relates to dental tools used to facilitate cavity repairs.

In dentistry it is a common practice to repair cavities by drilling out the decayed material to form a cavity preparation and filling the cavity preparation with some type of restoration material. When preparing cavities in two adjacent teeth with a common interproximal contact, it is typical practice to form the cavity preparations and then fill the preparations with a restoration material such as soft amalgam by arranging a flexible metal matrix band around each of the teeth, placing a triangular shaped wooden wedge in the interproximal space just above the gum line, filling the cavity preparations with the restoration material, permitting the filling material to condense or partially solidify, and removing the wedge and matrix bands. Since the bands are in common contact in the space between the adjacent teeth, care must be taken in removing each band to avoid dislodging the soft freshly placed restoration material. Since bands are typically used more than once, over time they develop dimples, wrinkles and other surface irregularities which tend to exacerbate this problem. To date the dentist has relied upon either his manual skill alone to remove each band, or has employed one of the dental tools used in packing the filler material into the cavity preparation to try to prevent the removal of the matrix band from dislodging the soft filler material. This technique is, at best, less than optimal since the tool can only be used to press down on a single tooth surface at any given time, and thus must be relocated on the surface of the other tooth prior to removing the second matrix band. As a result, matrix band removal from adjacent teeth remains one of the more time consuming procedures prone to manual error.

SUMMARY OF THE INVENTION

The invention comprises a dental tool having dual restoration material retainers for facilitating the removal of matrix bands from adjacent teeth while preventing dislodging of the restoration material during the band removal process.

The tool includes a shank terminating in a bifurcated end portion, each branch of the bifurcated end portion terminating in a working surface adapted to contact the filler material in the cavity preparation as well as a portion of the surrounding tooth surface. The inner edges of the working surfaces of the tool branches are separated by a gap having a width sufficiently large to accommodate the removal of a dental matrix band while maintaining tight common interproximal contact with the adjacent filler restoration. Each branch preferably has an inner surface terminating in the inner edge, the angle between the inner surface and the working surface being acute.

The preferred contour of the working end of each branch of the tool is generally a tear drop shape with a generally convex working surface so that the tool can be used at different approach angles to the tooth surface. Preferably, separate tools having different dimensions are installed on a common handle so that a single assembly can be used by the dentist for different sized teeth. In addition, the dimensions of the two branches of each tool can be slightly different to match the size progression of adjacent teeth. The tool can be fabricated from a range of materials, including stainless steel, titanium plastic and nylon.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a plan view of a preferred embodiment of the invention showing two tools mounted on a single common shaft;

FIG. 2 is a perspective view of the upper tool of FIG. 1;

FIG. 3 is a perspective view showing the hidden side of the lower tool of the FIG. 1 assembly;

FIG. 4 is an end view of the upper tool of the FIG. 1 assembly;

FIGS. 5A-5E are sequential schematic views illustrating the use of the preferred embodiment; and FIG. 6 is an enlarged partial side elevational view of the upper tool of the FIG. 1 assembly.

DESCRIPTION OF THE PREFERRED EMBODIMENTS

Turning now to the drawings. FIG. 1 illustrates a preferred embodiment of the invention. As seen in this Figure a dental instrument includes a central handle portion 11 an upper tool 12 and a lower tool 13. As best seen in FIG. 2, the upper tool 12 includes a shank 15 having a bifurcated end portion having a first branch leg 16 and a second branch leg 17. The branch legs 16 and 17 are joined at the end nearest shank 15 by a closed wall 18. Branch leg 16 terminates in a working end having a first working surface 19, while branch leg 17 terminates in a second working surface 20. As can be seen in FIG. 3, end 13 has a similar structure to end 12 (indicated by use of the primed reference numerals). but the specific dimensions are different to accommodate smaller teeth.

Again with reference to FIG. 2, branch leg 16 has an inner surface 21 extending from the wall portion 18 to an edge 22: while branch leg 17 has an inner wall surface 23 terminating in an edge 24. As best seen in FIG. 6, the angle between the branch leg inner wall surface and the working surface at the end of each branch legs forms an acute angle. In addition, the gap between each branch leg 16. 17 opens upwardly away from the working surfaces 19, 20.

Each tool 12, 13 is attached to handle 11 in any suitable fashion, for example by threading the free end of shank 15 to mate with a correspondingly threaded hole in one of the ends of handle 11.

FIGS. 5A-5E illustrate the use of the invention. FIG. 5A illustrates a pair of dental matrix bands 31, 32 installed about a pair of adjacent teeth 33, 34 and retained in place by a pair of matrix band holders 35, 36. A wooden triangular wedge 37 is installed in the interproximal space between teeth 31, 32, and each tooth 31, 32 has been provided with a suitable cavity preparation and the preparation has been filled with a restoration material, such as amalgam 38, 39. The object of the invention is to facilitate removal of the matrix bands 31. 32 without disturbing the placement of the amalgam 38. 39. This is accomplished as follows.

As shown in FIG. 5B, one of the tools, in this case tool 12, of the assembly is manipulated so that the working surfaces 19. 20 press onto the portion of filler material 38, 39 adjacent the interproximal gap above wedge 37 and also over surrounding portions of the occlusal surface of each tooth. Next, the band holders 35. 36 and the wedge 37 are removed, after which one of the matrix bands is maneuvered upwardly into the gap between branch legs 16. 17 of the tool (FIG. 5C). Once manipulated to the position shown in FIG. 5C. matrix band 31 can be completely withdrawn from the gap between branch legs 16 17. Thereafter, the second matrix band 32 is manipulated upwardly into the gap between branch legs 16, 17. (FIG. 5D). after which band 32 is completely removed (FIG. 5E). Throughout the process just described, the working ends 19. 20 of the tool 12 are maintained in firm contact with the occlusal surface of the filler material 38. 39 so that the interproximal spacing between the filler materials 38. 39 is maintained as tight as possible. Stated differently, the relatively narrow gap between the working edges 22, 24 of the tool (FIG. 6) insures that, during the removal of the bands 31. 32 the filler material 38. 39 will not be frictionally dislodged and carried upwardly by the surface of the band.

As will now be apparent, tools designed in accordance with the invention greatly facilitate the removal of the dental matrix bands in dual adjacent cavity preparation site procedures. Specifically, once the working surfaces 19, 20 are emplaced on the occlusal surfaces of the adjacent teeth, the tool can be merely held in firm contact with the restoration material and adjacent teeth surfaces while the matrix bands are removed. In addition, by forming the working ends of the tool in the generally convex, tear drop shape, the tool may be used at a variety of angles to approach the tooth, such as the upright angle illustrated in FIGS. 5A-5E or tilted to the rear or the front of the teeth. In order to accommodate variations in different tooth sizes, the dimensions of the two tools 12, 13 can be different. In addition, if desired the dimensions of the working surfaces 19, 20 can also be varied so that the curvature of one of the working ends can be made slightly smaller than the other to accommodate adjacent teeth of different sizes. Lastly, the tools 12, 13 can be fabricated from a variety of materials including metals, such as stainless steel and titanium, plastics and nylon.

While the above provides a full and complete disclosure of the invention, various modifications, alternate constructions and equivalents will occur to those skilled in the art. Therefore, the above should not be construed as limiting the invention, which is defined by the appended claims.

What is claimed is:

1. A dental tool for assisting in cavity repair in two adjacent teeth by facilitating removal of matrix bands therefrom after installation of filler restoration material, said tool comprising a shank terminating in a bifurcated end portion, each branch of said bifurcated end portion terminating in a working surface having an inner edge, the inner edges of the working surfaces being separated by a gap having a width sufficiently large to accommodate a dental matrix band and sufficiently narrow to enable the working surfaces to maintain tight common interproximal contact with the filler restoration material in adjacent teeth.

2. The invention of claim 1 wherein each branch has an inner surface terminating in said inner edge, and wherein the angle between said inner surface and said working surface is acute.

3. The invention of claim 1 wherein the working surface of each end portion is generally convex.

4. The invention of claim 1 wherein the dimensions of the working surface of one of said branches are different from the dimensions of the working surface of the other branch.

* * * * *